(12) United States Patent
Harlick et al.

(10) Patent No.: US 8,709,770 B2
(45) Date of Patent: Apr. 29, 2014

(54) PROCESS FOR IMPROVING THE HYDROLYSIS OF CELLULOSE IN HIGH CONSISTENCY SYSTEMS USING ONE OR MORE UNMIXED AND MIXED HYDROLYSIS REACTORS

(75) Inventors: Peter J. E. Harlick, Metcalfe (CA); Wei Zheng, Ottawa (CA)

(73) Assignee: Iogen Energy Corporation, Ontario (CA)

( * ) Notice: Subject to any disclaimer, the term of this patent is extended or adjusted under 35 U.S.C. 154(b) by 194 days.

(21) Appl. No.: 13/216,368

(22) Filed: Aug. 24, 2011

(65) Prior Publication Data

US 2012/0052534 A1 Mar. 1, 2012

Related U.S. Application Data

(60) Provisional application No. 61/378,523, filed on Aug. 31, 2010.

(51) Int. Cl.
*C12P 7/10* (2006.01)
(52) U.S. Cl.
USPC ........................................................ 435/165
(58) Field of Classification Search
USPC ............... 435/105, 165, 289.1, 293.1; 127/37
See application file for complete search history.

(56) References Cited

U.S. PATENT DOCUMENTS

| | | | | |
|---|---|---|---|---|
| 4,409,329 | A | * | 10/1983 | Silver ............................ 435/105 |
| 5,258,293 | A | | 11/1993 | Lynd et al. |
| 5,411,594 | A | * | 5/1995 | Brelsford ........................ 127/37 |
| 5,733,758 | A | | 3/1998 | Nguyen |
| 5,837,506 | A | | 11/1998 | Lynd et al. |
| 5,888,806 | A | | 3/1999 | Nguyen |
| 7,598,069 | B2 | | 10/2009 | Felby et al. |
| 7,754,457 | B2 | * | 7/2010 | Foody et al. .................. 435/165 |
| 7,993,463 | B2 | * | 8/2011 | Griffin et al. ................... 127/37 |
| 2009/0035826 | A1 | * | 2/2009 | Tolan et al. ..................... 435/99 |
| 2009/0098616 | A1 | | 4/2009 | Burke et al. |
| 2010/0190226 | A1 | * | 7/2010 | Foody et al. .................. 435/162 |
| 2010/0221819 | A1 | | 9/2010 | Foody et al. |
| 2012/0237983 | A1 | * | 9/2012 | Harlick ............................ 435/99 |

FOREIGN PATENT DOCUMENTS

| | | |
|---|---|---|
| WO | WO 02/070753 A2 | 9/2002 |
| WO | WO 2005/118828 A1 | 12/2005 |
| WO | WO 2006/063467 A1 | 6/2006 |
| WO | WO 2009/045651 A1 | 4/2009 |
| WO | WO 2010/022511 A1 | 3/2010 |

OTHER PUBLICATIONS

Chen et al., "Effect of Sugar Consumption on Ethanol Fermentation in a Tower Fermentor Packed with Self-Aggregating Yeast", Applied Biochemistry and Biotechnology, vol. 39, No. 40 (1993) 491-508.
Kim et al., "Plug-Flow Reactor for Continuous Hydrolysis of Glucans and Xylans from Pretreated Corn Fiber", Energy and Fuels, vol. 19, No. 5 (2005) 2189-200.
Kleijntjens et al., "A Continuous Thermophilic Cellulose Fermentation in an Upflow Reactor by a *Clostridium thermocellum*-Containing Mixed Culture", Biotechnology Letters, vol. 8, No. 9 (1986) 667-72.
Levenspiel, "Chemical Reaction Engineering", Third Edition, John Wiley and Sons, Chapter 5 (1999) 92-118.
Szijártó et al., "Liquefaction of hydrothermally pretreated wheat straw at high-solids content by purified Trichoderma enzymes", Bioresource Technology, vol. 102, No. 2 (2010) 1968-74.
Tengborg et al., "Influence of Enzyme Loading and Physical Parameters on the Enzymatic Hydrolysis of Steam-Pretreated Softwood", Biotechnol. Prog., vol. 17, No. 1 (2001) 110-17.

* cited by examiner

*Primary Examiner* — Ralph Gitomer
(74) *Attorney, Agent, or Firm* — Fitzpatrick, Cella, Harper & Scinto (57) ABSTRACT

Provided is a process for the enzymatic hydrolysis of cellulose to produce glucose from a pretreated cellulosic feedstock. The process comprises providing an aqueous slurry of the pretreated cellulosic feedstock that has a water content that is less than about 140% of the maximum water holding capacity of the pretreated cellulosic feedstock. The aqueous slurry of the pretreated cellulosic feedstock is fed to one or more unmixed hydrolysis reactors and hydrolyzed with cellulase enzymes therein. In the unmixed hydrolysis reactor(s), the cellulase enzymes hydrolyze a portion of the cellulose to produce soluble sugars, thereby producing a mixture of partially hydrolyzed cellulose containing soluble sugars. The hydrolysis of the cellulose to glucose is continued by feeding the mixture of partially hydrolyzed cellulose to one or more mixed hydrolysis reactors. Also provided are systems for carrying out the foregoing enzymatic hydrolysis.

20 Claims, 7 Drawing Sheets

Configuration 1:

Configuration 2:

Configuration 3:

PROCESS FOR IMPROVING THE HYDROLYSIS OF CELLULOSE IN HIGH CONSISTENCY SYSTEMS USING ONE OR MORE UNMIXED AND MIXED HYDROLYSIS REACTORS

CROSS-REFERENCE TO RELATED APPLICATIONS

This application claims the priority benefit of a provisional application No. 61/378,523, filed Aug. 31, 2010, which is incorporated herein by reference.

TECHNICAL FIELD

The present invention relates to an improved method for producing fermentable sugar from a cellulosic feedstock.

BACKGROUND

Much attention and effort has been applied in recent years to the production of fuels and chemicals, primarily ethanol, from cellulosic feedstocks, such as agricultural wastes and forestry wastes, due to their low cost and wide availability. These agricultural and forestry wastes are typically burned and landfilled; thus, using these cellulosic feedstocks for ethanol production offers an attractive alternative to disposal.

The first chemical processing step for converting cellulosic feedstock to ethanol or other fermentation products usually involves pretreatment of the feedstock. The purpose of the pretreatment is to increase the cellulose surface area, with limited conversion of the cellulose to glucose. Pretreatment of the feedstock can be achieved using an acid pretreatment conducted under conditions that hydrolyse the hemicellulose component of the feedstock, followed by enzymatic hydrolysis of the cellulose remaining in the pretreated cellulosic feedstock with cellulase enzymes. Enzymatic hydrolysis is typically conducted in one or more dilute mixed batch reactors under controlled pH, temperature and mixing conditions.

The cellulase enzymes utilized to hydrolyze the cellulose to glucose include a mix of enzymes including exo-cellobiohydrolases (CBH), endoglucanases (EG) and beta-glucosidases. The CBH and EG enzymes catalyze the hydrolysis of the cellulose (β-1,4-D-glucan linkages). The CBH enzymes, CBHI and CBHII (also known as Cel7 and Cel6 according to Glycoside Hydrolase family designations), act on the ends of the glucose polymers in cellulose microfibrils and liberate cellobiose, while the EG enzymes (including EGI, EGII, EGIII and EGV, also known as Cel7, Cel5, Cel12 and Cel45, respectively) act at random locations on the cellulose. Together, the cellulase enzymes hydrolyze cellulose to cellobiose, which, in turn, is hydrolyzed to glucose by beta-glucosidase (beta-G).

In addition to CBH, EG and beta-glucosidase, there are several accessory enzymes that aid in the enzymatic digestion of cellulose (see co-owned WO 2009/026722 (Scott), which is incorporated herein by reference, and Harris et al., 2010, Biochemistry, 49:3305-3316). These include EGIV, also known as Cel61, swollenin, expansin, lucinen and cellulose-induced protein (Cip). Glucose can be enzymatically converted to the dimers gentiobiose, sophorose, laminaribiose and others by beta-glucosidase via transglycosylation reactions.

In conventional hydrolysis reactors, mixing is provided by mechanical mixers such as top-mounted, side-mounted, or bottom-mounted impellers, agitators or eductors; rapid movement of liquid slurry streams pumped into or through the vessel; and/or introducing or generating gases or vapours in the vessel. Moreover, reactors are known that employ periodic mixing as the slurry passes through mixing zones along the length of the reactor (see U.S. Pat. No. 5,733,758 (Nguyen) discussed below).

The fermentation to produce ethanol from the glucose is typically carried out with a *Saccharomyces* spp. strain. Recovery of the ethanol is achieved by distillation and the ethanol is further concentrated by molecular sieves.

The addition of water to the incoming feedstock to form a slurry facilitates the transportation and mechanical handling of the cellulosic feedstock. The slurry consists of cellulosic feedstock pieces or particles in water. Typically, the mass of water present is at least 5 to 25 times the mass of feedstock solids present for the slurry to flow uniformly.

However, the processing of slurries containing such high water content has certain drawbacks in plant operations. For example, during acid pretreatment, the high water content in the incoming slurry requires a large amount of steam for the heat-up, as well as acid. Moreover, large volumes of water in the slurry result in increases in equipment size, which, in turn, increases capital cost.

WO 2010/022511 (Anand et al.) discloses a process involving the removal of a significant amount of water from a cellulosic feedstock slurry by a pressurized screw press prior to its heat-up by steam in a pretreatment reactor. Advantageously, due to the high solids content attained by pressing, less liquid needs to be heated, thereby reducing the amount of steam required during the subsequent pretreatment. Moreover, a concentrated slurry can also reduce the amount of acid or alkali that is needed to catalyze the hydrolysis of the feedstock.

However, despite the foregoing advantages associated with high solids content slurries, their handling downstream of pretreatment can pose problems. For instance, in order for conventional stirred reactors to mix the highly viscous slurry effectively during enzymatic hydrolysis, a very large power input is required. Moreover, specialized high solids consistency pumps are needed to convey the high solids content slurry through the system. These requirements can significantly increase the capital and operating costs of the hydrolysis process.

There has been much effort devoted to hydrolysis reactor development, but it has focused primarily on dilute systems. WO 2006/063467 (Foody et al.) discloses the use of an unmixed upflow hydrolysis reactor for the enzymatic hydrolysis of a pretreated cellulosic feedstock with cellulase enzymes. The hydrolysis is conducted so that the upward velocity of the slurry is slow and the solid particles, which are denser than the bulk slurry, tend to flow upward more slowly than the liquor. The slow upward flow of the cellulose-containing solid particles retains the cellulose-containing solids and the bound cellulase enzymes in the reactor for a longer time than the liquid, thereby improving the conversion of the cellulose to glucose.

U.S. Pat. No. 5,258,293 (Lynd) discloses a method in which lignocellulosic feedstock and microorganisms are continuously introduced into a reaction vessel. Fluid is also continuously added from the bottom of the reaction vessel, but no mechanical agitation of the slurry occurs. As the reaction progresses, the lignocellulosic feedstock being digested tends to accumulate in a spatially non-homogenous layer, while the ethanol product rises to a top layer, where it is removed. The insoluble substrate accumulates in a bottom layer and can be withdrawn from the vessel. This arrangement results in a differential retention of the fermenting substrate, which allows for increased residence time in the reactor vessel.

In another approach, disclosed in U.S. Pat. No. 5,837,506 (Lynd), ethanol is produced using an intermittently agitated, perpetually fed bioreactor. Lignocellulosic slurry and microorganisms are added to a reactor; the mixture is then agitated, either by mechanical means or by fluid recirculation, for a specific time interval, after which it is allowed to settle. Ethanol is then removed from a top portion of the reactor, additional substrate is added, and the cycle continues.

In a similar method, Kleijntjens et al. (1986, Biotechnology Letters, 8:667-672) utilize an upflow reactor to ferment cellulose-containing substrate in the presence of C. thermocellum. The substrate slurry settles to form an aggregated fibre bed, which is accelerated by slow mechanical stirring. Substrate is added periodically, while liquid is continuously fed to the reactor. Ethanol product accumulates in a top layer, where it is removed from the reactor.

However, the methods described in U.S. Pat. Nos. 5,258,293 and 5,837,506 and Kleijntjens et al. (supra) may not be suitable for concentrated systems.

WO 2009/045651 (Hennessey et al.) discloses a process for saccharifying pretreated biomass at a high dry weight to produce fermentable sugars. The process of the invention uses a fed batch reactor system including multiple size reduction steps and thorough mixing in a standard vertical, agitated tank. Biomass is introduced into the vertical reactor tank equipped with an overhead agitator system such as a motor and shaft with one or more impellers.

US 2009/0098616 (Burke et al.) discloses a process in which a fine particulate stream of feedstock is subjected to a two-stage enzymatic hydrolysis process. The two-stage process allows for a reduction in the viscosity of the feedstock in the first stage and the production of a process stream that is rich in fermentable sugars in the second stage. Viscosity reduction is carried out in stirred reaction vessels and is thought to occur by the hydrolysis of xylan to soluble oligomers.

U.S. Pat. No. 5,733,758 (Nguyen) discloses an approach using a tower hydrolysis reactor comprising alternating mixed and unmixed zones. The solids loading of the slurry introduced to the hydrolysis is greater than 10 wt %. The slurry is moved upward in plug flow through the reactor and is intermittently mixed in the mixing zones, thus preventing channeling of liquid and ensuring uniform heat and mass transfer. As set forth therein, frequent and high initial mixing at the beginning of the hydrolysis when viscosity of the slurry is high is required to obtain as high a hydrolysis rate as is obtainable by continuous mixing.

U.S. Pat. No. 7,598,069 (Felby) discloses a method for hydrolyzing polysaccharide containing biomasses having a final dry matter content of above 20% involving mixing by a free fall type mixing that provides mechanical degradation of the biomass during hydrolysis. The mixer may be a drum mixer, a mixer with a rotary axis lifting the biomass or a similar mixing device utilizing a free fall principle. Such mixers are typically very large and significant power is required to rotate the vessel.

Despite these efforts, there is a need for more efficient and cost effective processes for enzymatically hydrolyzing cellulose in concentrated systems to obtain fermentable sugar. In particular, there is a need in the art to further reduce capital and operating costs associated with such processes so as to make them commercially viable.

SUMMARY OF THE INVENTION

The present invention overcomes several disadvantages of the prior art by taking into account the difficulties encountered in steps carried out during the processing of cellulosic feedstock to obtain fermentable sugar.

It is an object of the invention to provide an improved method for producing fermentable sugar from a cellulosic feedstock.

According to a first aspect of the invention, there is provided a process for the enzymatic hydrolysis of cellulose to produce glucose from a pretreated cellulosic feedstock, the process comprising: (i) providing an aqueous slurry of the pretreated cellulosic feedstock, which aqueous slurry has a water content that is less than about 140% of the maximum water holding capacity of the pretreated cellulosic feedstock; (ii) introducing the aqueous slurry of the pretreated cellulosic feedstock to an unmixed hydrolysis reactor; (iii) adding cellulase enzymes to the aqueous slurry before the step of introducing (step ii), during the step of introducing (step ii) or to the unmixed hydrolysis reactor, or a combination thereof, wherein, in the unmixed hydrolysis reactor, the cellulase enzymes hydrolyze a portion of the cellulose to produce soluble sugars, thereby producing a mixture of partially hydrolyzed cellulose containing soluble sugars; (iv) continuing the hydrolysis of the cellulose to glucose by feeding the mixture of partially hydrolyzed cellulose containing soluble sugars to a mixed hydrolysis reactor that effects mixing of the mixture or a hydrolysis system comprising mixed hydrolysis reactors that effects mixing of the mixture; and (v) withdrawing a stream comprising glucose and unreacted cellulose from the mixed hydrolysis reactor or the hydrolysis system of step (iv).

According to a second aspect of the invention, there is provided a process for the enzymatic hydrolysis of cellulose to produce glucose from a pretreated cellulosic feedstock, the process comprising: (i) providing an aqueous slurry of the pretreated cellulosic feedstock, which aqueous slurry has a water content that is less than about 140% of the maximum water holding capacity of the pretreated cellulosic feedstock; (ii) introducing the aqueous slurry of the pretreated cellulosic feedstock to a system of unmixed hydrolysis reactors; (iii) adding cellulase enzymes to the aqueous slurry before the step of introducing (step ii), during the step of introducing (step ii), or to one or more unmixed hydrolysis reactor in the system, or a combination thereof, wherein the cellulase enzymes hydrolyze a portion of the cellulose to produce soluble sugars in the system of unmixed hydrolysis reactors, thereby producing a mixture of partially hydrolyzed cellulose containing soluble sugars; (iv) continuing the hydrolysis of the cellulose to glucose by feeding the mixture of partially hydrolyzed cellulose containing soluble sugars to one or more hydrolysis reactors that effect mixing of the mixture; and (v) withdrawing a stream comprising glucose and unreacted cellulose from the one or more hydrolysis reactors of step (iv).

According to an embodiment of either of the foregoing aspects of the invention, the water content of the aqueous slurry is between about 40% and about 140%, or between about 60% and about 120% of the maximum water holding capacity of the pretreated cellulosic feedstock.

According to a further embodiment of the invention, the portion of the cellulose hydrolyzed in the unmixed reactor is between about 10 wt % and about 70 wt %, or between about 15 wt % and about 40 wt %. In yet further embodiments of the invention, the portion of the cellulose hydrolyzed in the unmixed reactor is between about 25 wt % and about 70 wt %, or between about 35 wt % and about 70 wt %. The soluble sugars in the mixture of partially hydrolyzed cellulose after the unmixed hydrolysis comprise glucose, cellobiose, gentiobiose, glucose oligomers, or a combination thereof.

Preferably, the cellulase enzyme contains beta-glucosidase.

The unmixed hydrolysis reactor may be a batch, fed-batch or continuous reactor with a height-to-diameter ratio of about 0.2:1.0 to about 5.0:1.0.

According to a third aspect, the present invention provides system for hydrolyzing cellulose to glucose, the system comprising: (i) one or more unmixed hydrolysis reactors for receiving and partially hydrolyzing an aqueous slurry of the pretreated cellulosic feedstock with cellulase enzymes so as to produce a mixture of partially hydrolyzed cellulose; and (ii) one or more downstream mixed hydrolysis reactors for continuing the hydrolysis of the mixture of the partially hydrolyzed cellulose to glucose.

According to a fourth aspect of the invention, there is provided a system for hydrolyzing a cellulosic feedstock slurry to produce glucose, the system comprising: (i) a dewatering device for receiving and dewatering the cellulosic feedstock slurry; (ii) a pretreatment reactor upstream or downstream of the dewatering device for receiving and pretreating the cellulosic feedstock slurry to produce a pretreated cellulosic feedstock; (iii) one or more unmixed hydrolysis reactors for receiving and partially hydrolyzing the pretreated cellulosic feedstock with cellulase enzymes so as to produce a mixture of partially hydrolyzed cellulose; and (iv) one or more mixed hydrolysis reactors downstream of the unmixed hydrolysis reactors for continuing the hydrolysis of the mixture of the partially hydrolyzed cellulose to produce glucose.

According to one embodiment of the invention, the unmixed hydrolysis reactor in the system is a plug-flow reactor.

The present invention can provide numerous benefits over conventional processes for converting concentrated cellulosic slurries to fermentable sugar using cellulase enzymes. By reducing the viscosity of a pretreated cellulosic feedstock in an unmixed hydrolysis reactor(s), the power input associated with mixing in the downstream mixed reactors can be significantly reduced. Moreover, the use of specialized high solids consistency pumps to convey the high solids content slurry through the system can be minimized.

Reducing the capital and operating costs associated with handling concentrated, highly viscous slurries during enzymatic hydrolysis could be a significant step forward with respect to commercialization of producing fermentable sugar from cellulosic feedstocks.

DETAILED DESCRIPTION OF THE INVENTION

The following description is of a preferred embodiment by way of example only and without limitation to the combination of features necessary for carrying the invention into effect. The headings provided are not meant to be limiting of the various embodiments of the invention. Terms such as "comprises", "comprising", "comprise", "includes", "including" and "include" are not meant to be limiting. In addition, the use of the singular includes the plural, and "or" means "and/or" unless otherwise stated. Unless otherwise defined herein, all technical and scientific terms used herein have the same meaning as commonly understood by one of ordinary skill in the art.

Feedstock Processing Prior to Pretreatment

The feedstock for the process is a cellulosic material. By the term "cellulosic feedstock", it is meant any type of plant biomass such as, but not limited to, cultivated crops such as, but not limited to grasses, for example, but not limited to, C4 grasses, such as switch grass, cord grass, rye grass, miscanthus, reed canary grass, or a combination thereof, sugar processing residues, for example, but not limited to, baggase, such as sugar cane bagasse, beet pulp, or a combination thereof, agricultural residues, for example, but not limited to, soybean stover, corn stover, rice straw, sugar cane straw, rice hulls, barley straw, corn cobs, wheat straw, canola straw, oat straw, oat hulls, corn fiber, or a combination thereof, forestry biomass for example, but not limited to, recycled wood pulp fiber, sawdust, hardwood, for example aspen wood, softwood, or a combination thereof. Furthermore, the cellulosic feedstock may comprise cellulosic waste material or forestry waste materials such as, but not limited to, newsprint, cardboard and the like. Cellulosic feedstock may comprise one species of fiber or, alternatively, cellulosic feedstock may comprise a mixture of fibers that originate from different cellulosic feedstocks. In addition, the cellulosic feedstock may comprise fresh cellulosic feedstock, partially dried cellulosic feedstock, fully dried cellulosic feedstock, or a combination thereof. Moreover, new lignocellulosic feedstock varieties may be produced from any of those species listed above by plant breeding or by genetic engineering.

Cellulosic feedstocks comprise cellulose in an amount greater than about 20%, more preferably greater than about 30%, more preferably greater than about 40% (w/w). For example, the cellulosic material may comprise from about 20% to about 50% (w/w) cellulose, or any amount therebetween. Furthermore, the cellulosic feedstock comprises lignin in an amount greater than about 10%, more typically in an amount greater than about 15% (w/w). The cellulosic feedstock may also comprise small amounts of sucrose, fructose and starch.

Cellulosic feedstocks that have particle sizes of less than about 6 inches may not require size reduction. That is, such feedstocks may simply be slurried in water and then pumped to downstream stages of the process. For feedstocks of larger particle sizes, the cellulosic feedstock is generally subjected to size reduction by methods including, but not limited to, milling, grinding, agitation, shredding, compression/expansion, or other types of mechanical action. Size reduction by mechanical action can be performed by any type of equipment adapted for the purpose, for example, but not limited to, hammer mills, tub-grinders, roll presses, refiners and hydra-pulpers. Preferably, at least 90% by volume of the particles produced from the size reduction may have a length less than between about 1/16 and about 6 in. The preferable equipment for the particle size reduction is a hammer mill, a refiner or a roll press as disclosed in WO 2006/026863, which is incorporated herein by reference.

Before, during or subsequent to size reduction, the feedstock can be slurried in water, which allows the feedstock to be pumped. The desired weight ratio of water to dry cellulosic feedstock solids in the slurry is determined by factors such as pumpability, pipe-line requirements, and other practical considerations.

The solids concentration of the aqueous slurry of the cellulosic feedstock is expressed as the undissolved solids (UDS) concentration. Prior to pretreatment, the cellulosic feedstock slurry UDS is typically about 3% to about 30% or about 4% to about 20%.

The weight ratio of dry solids to aqueous slurry is determined by the UDS procedure of Example 1.

The feedstock fiber may be soaked with water or an aqueous solution comprising acid. Soaking may be carried out by introducing the cellulosic feedstock to a tank where it is mixed with hot water at relatively low solids consistency. Generally, the cellulosic feedstock will be subjected to size reduction prior to its introduction to the tank where soaking takes place. Moreover, the cellulosic feedstock may be leached as set forth in WO 02/070753 (Griffin, which is incorporated herein by reference).

After slurrying, leaching and/or soaking, the cellulosic feedstock may subsequently be dewatered by any suitable technique. For instance, dewatering may be effected by utilizing devices that remove water under pressure from the aqueous feedstock slurry. Dewatering devices suitable for use in the invention includes pressurized screw presses, such as those described in WO 2010/022511 (incorporated herein by reference) and pressurized filters. The dewatering process optionally includes a pre-draining zone in order to drain out water from the feedstock slurry at atmospheric pressure or higher. This dewatered feedstock slurry is then sent to one or more devices for dewatering the slurry under pressure. Water expressed from the cellulosic feedstock by the dewatering step may be reused in the process.

Pretreatment of the Cellulosic Feedstock

The cellulosic feedstock is subjected to pretreatment prior to enzymatic hydrolysis with cellulase enzymes. The pretreatment is generally intended to deliver a sufficient combination of mechanical and chemical action so as to disrupt the fiber structure of the cellulosic feedstock and increase the surface area of the feedstock to make it accessible to cellulase enzymes. Preferably, the pretreatment is performed so that a high degree of hydrolysis of the hemicellulose and only a small amount of conversion of cellulose to glucose occurs. The cellulose is hydrolyzed to glucose in a subsequent step that uses cellulase enzymes. In one example of the invention, a dilute mineral acid, at a concentration from about 0.02% (w/w) to about 5% (w/w), or any amount therebetween, (measured as the percentage weight of pure acid in the total weight of dry feedstock plus aqueous solution) is used for the pretreatment.

The acid may be sulfuric acid, sulfurous acid, hydrochloric acid or phosphoric acid. Preferably, the acid is sulfuric acid. The amount of acid added to the cellulosic feedstock may vary, but should be sufficient to achieve a final concentration of acid of about 0.02% to about 2% w/w, or any amount therebetween. The resulting pH of the feedstock is about pH 0.4 to about pH 3.5, or any pH range therebetween.

The acid pretreatment is preferably carried out at a maximum temperature of about 160° C. to about 280° C. However, in practice, there will be a time delay in the pretreatment process before the feedstock reaches this temperature range. The above temperatures correspond to those values reached after sufficient application of heat to reach a temperature within this range. The time that the feedstock is held at this temperature may be about 6 seconds to about 3600 seconds, or about 15 seconds to about 750 seconds or about 30 seconds to about 240 seconds.

The pretreatment is typically carried out under pressure. For example, the pressure during pretreatment may be between about 50 and about 700 psig or between about 75 and about 600 psig, or any pressure range therebetween.

The feedstock may be heated with steam during or prior to pretreatment. Without being limiting, one method to carry this out is to use low pressure steam to partially heat the feedstock, which is then pumped to a heating train of several stages. Other means may be employed to heat the feedstock, such as commercially available mixing devices designed for introducing steam and optionally acid through spray nozzles.

One method of performing acid pretreatment of the feedstock is steam explosion using the process conditions set out in U.S. Pat. No. 4,461,648 (Foody, which is herein incorporated by reference). Another method of pretreating the feedstock slurry involves continuous pretreatment, meaning that the cellulosic feedstock is pumped through a reactor continuously. Continuous acid pretreatment is familiar to those skilled in the art; see, for example, U.S. Pat. No. 5,536,325 (Brink); WO 2006/128304 (Foody and Tolan); and U.S. Pat. No. 4,237,226 (Grethlein), which are each incorporated herein by reference. Additional techniques known in the art may be used as required such as the process disclosed in U.S. Pat. No. 4,556,430 (Converse et al.; which is incorporated herein by reference).

The acid pretreatment produces a composition comprising an acid pretreated feedstock. Sugars produced by the hydrolysis of hemicellulose during pretreatment are generally present in the composition and include xylose, glucose, arabinose, mannose, galactose or a combination thereof.

The aqueous phase of the pretreated feedstock composition may also contain the acid added during the pretreatment. When sulfuric acid is the acid utilized in the pretreatment, the composition comprising the pretreated feedstock additionally contains sulfate and/or bisulfate salts.

The composition comprising acid pretreated feedstock will also comprise acetic acid produced during acid pretreatment. The concentration of acetic acid in this stream may be between 0.1 and 20 g/L. Additional organic acids may be liberated during pretreatment, including galacturonic acid, formic acid, lactic acid and glucuronic acid. Pretreatment may also produce dissolved lignin and inhibitors such as furfural and hydroxymethyl furfural (HMF). Accordingly, the composition comprising acid pretreated feedstock may also contain these components.

According to one exemplary embodiment of the invention, the soluble components of the pretreated feedstock composition are separated from the solids. This separation may be carried out by washing the pretreated feedstock composition with an aqueous solution to produce a wash stream, and a solids stream comprising the unhydrolyzed, pretreated feedstock. Alternatively, the soluble component is separated from the solids by subjecting the pretreated feedstock composition to a solids-liquid separation using known methods such as centrifugation, microfiltration, plate and frame filtration, cross-flow filtration, pressure filtration, vacuum filtration and the like. Optionally, a washing step may be incorporated into the solids-liquids separation. The separated solids, which contain cellulose, may then be sent to enzymatic hydrolysis with cellulase enzymes in order to convert the cellulose to glucose. The enzymatic hydrolysis of cellulose using cellulase enzymes is described in more detail hereinafter.

The separated soluble component from the above-described separation, which includes the sugars released during pretreatment, the pretreatment acid and other soluble components, may then be fermented using a microorganism capable of fermenting the sugars derived from the hemicellulose component of the feedstock.

Pretreatment may also be carried out under alkaline conditions. Examples of suitable alkaline pretreatment processes include ammonia fiber expansion (AFEX) or dilute ammonia pretreatment.

According to the AFEX process, the cellulosic biomass is contacted with ammonia or ammonium hydroxide, which is typically concentrated, in a pressure vessel. The contact is maintained for a sufficient time to enable the ammonia or ammonium hydroxide to swell (i.e., decrystallize) the cellulose fibers. The pressure is then rapidly reduced which allows the ammonia to flash or boil and explode the cellulose fiber structure. The flashed ammonia may then be recovered according to known processes. The AFEX process may be run at about 20° C. to about 150° C. or at about 20° C. to about 100° C. and all temperatures therebetween. The duration of this pretreatment may be about 1 minute to about 20 minutes, or any time therebetween.

Dilute ammonia pretreatment utilizes more dilute solutions of ammonia or ammonium hydroxide than AFEX. Such a pretreatment process may or may not produce any monosaccharides. Dilute ammonia pretreatment may be conducted at a temperature of about 100 to about 150° C. or any temperature therebetween. The duration for such a pretreatment may be about 1 minute to about 20 minutes, or any time therebetween.

Subsequent to pretreatment, the pretreated feedstock slurry is typically cooled prior to enzymatic hydrolysis to decrease it to a temperature at which the cellulase enzymes are active. It should be appreciated that cooling of the feedstock can occur in a number of stages utilizing flashing, heat exchange or other suitable means. In one embodiment of the invention, the pretreated feedstock is cooled to temperatures of about 100° C. and below before enzymatic hydrolysis.

Unmixed Enzymatic Hydrolysis

The aqueous slurry of the pretreated cellulosic feedstock is fed to an unmixed hydrolysis reactor or to a system of unmixed hydrolysis reactors to produce a mixture of partially hydrolyzed cellulose, which is subsequently fed to one or more hydrolysis reactors that hydrolyze the feedstock with mixing, as described hereinafter. In the unmixed reactor or reactor system, the enzymatic hydrolysis of the cellulose reduces the viscosity of the pretreated cellulosic feedstock. Advantageously, by reducing the viscosity of the pretreated feedstock by enzymatic hydrolysis, the power requirements associated with mixing are reduced during hydrolysis of the mixture of partially hydrolyzed cellulose in the subsequent mixed hydrolysis reactor(s).

Viscosity measurements are dependent on the characteristics of the fluid being measured. Pretreated slurry exhibits characteristics which can be defined as non-Newtonian in nature, meaning that the viscosity of the slurry is not constant and is a function of the energy imparted on it. The energy imparted on the slurry may be interpreted as the local shear rate.

As such, the quantitative measure of the viscosity of the pretreated feedstock must refer to the shear rate at which the viscosity was measured. For example, at low shear rates, pretreated slurries exhibit higher viscosities than those determined at high shear rates.

For the purposes of this specification, the term "viscosity" is used in the qualitative sense to denote thick or thin slurries.

By the term "unmixed hydrolysis reactor", it is meant a reactor suitable for conducting an enzymatic hydrolysis with cellulase enzymes therein that does not carry out any active mixing of its contents as is typically employed in mixed hydrolysis reactors. Although the unmixed reactor of the present invention may operate with a certain amount of localized mixing due to the introduction and withdrawal of liquid and solids from the system, such localized mixing does not result in any significant dispersal or blending of the reactor contents, as would occur in mixed reactors. For example, a small amount of localized mixing may occur at the bottom of an unmixed downflow reactor due to the action of a rotary bottom scraper or other devices employed for removing the reactor contents. Similarly, if the unmixed reactor is an upflow reactor, a small amount of localized mixing may occur at the top of the unmixed reactor due to the withdrawal of the slurry. The power required for the discharge of the slurry is less than 5%, 3% or 1% of the power required to fully mix the slurry using a mixed reactor of conventional hydrofoil impeller design.

By contrast, in conventional mixed hydrolysis reactors, mixing is provided by mechanical mixers such as top-mounted, side-mounted, or bottom-mounted impellers, agitators or eductors; rapid movement of liquid slurry streams pumped into or through the vessel; and/or introducing or generating gases or vapours in the vessel. Moreover, reactors are known that employ periodic mixing (also referred to herein as "intermittent mixing") as the slurry passes through mixing zones along the length of the reactor (see U.S. Pat. No. 5,888,806 (Nguyen)).

The unmixed hydrolysis may be a batch, fed-batch or a continuous operation.

A suitable height-to-diameter ratio of an unmixed batch or continuous hydrolysis reactor is between about 0.2:1.0 to about 5.0:1.0, or any ratio therebetween.

The number of unmixed hydrolysis reactors in the system depends on the cost of the reactors, the volume of the aqueous slurry, and other factors. For a commercial-scale plant, the typical number of unmixed hydrolysis reactors may be, for example, 1 to 10.

The unmixed reactors can be in a consecutive or parallel configuration. Those of ordinary skill in the art could readily select a suitable option by weighing the advantages and disadvantages of each design scheme.

According to embodiments of the invention, the aqueous slurry of the pretreated cellulosic feedstock has a water content (w/w) that is less than about 140% of the maximum water holding capacity of the pretreated cellulosic feedstock. That is, the pretreated cellulosic feedstock may contain some free water or no free water. The invention encompasses any range of water content of the pretreated cellulosic feedstock having numerical limits 40, 50, 60, 70, 80, 90, 100, 110, 120, 130 or 140% of the maximum water holding capacity.

In one embodiment of the invention, the pretreated cellulosic feedstock has a water content of between 40% and 140% of the maximum water holding capacity, or between 50% and 140%, or between 60% and 140%, or between 70% and 140%, or between 80 and 140% of the maximum water holding capacity, or any range therebetween. In another embodiment of the invention, the pretreated cellulosic feedstock has a water content of between 40% and 130%, or between 40% and 120%, or between 40% and 110%, or between 40% and 100%, or between 40% and 90% of the maximum water holding capacity, or any range therebetween.

Whether or not the aqueous slurry contains free water can be determined by measuring the maximum water holding capacity of the pretreated cellulosic feedstock as set forth in Example 3. The maximum water holding capacity of a pretreated cellulosic feedstock is determined by measuring the amount of water which may be absorbed by a known mass of pretreated cellulosic feedstock until the point at which additional water added to the feedstock is free water.

The pretreated cellulosic feedstock slurry introduced to the unmixed hydrolysis reactor has between about 12 wt % and about 40 wt % undissolved solids (UDS) or any range therebetween. In another embodiment of the invention, the pretreated cellulosic feedstock slurry has between about 14 wt % and about 28 wt % UDS, or any range therebetween or between about 18 wt % and about 24 wt % UDS. The range may contain numerical limits of 12, 13, 14, 15, 16, 17, 18, 19, 20, 21, 22, 23, 24, 25, 26, 27, 28, 29, 30, 31, 32, 33, 34, 35, 36, 37, 38, 39 or 40% (w/w). The undissolved solids content is based on dry weight of the solids and is measured according to the procedure set forth in Example 1.

The foregoing solids consistency range may be attained by dewatering various feedstock preparations prior to pretreatment including, for example, a soaked feedstock, a leached feedstock or a feedstock slurry. Alternatively, a dewatering step can be conducted after pretreatment on the pretreated feedstock slurry. Without being limiting, suitable dewatering devices include screw presses, filters, centrifuges and extruders. In a further embodiment, the slurry may be prepared by the addition of sufficient amounts of water or aqueous solution to a feedstock that has been subjected to particle size reduction to attain a solids content in this range (see for example, WO 2009/125292 that is incorporated herein by reference).

The enzymatic hydrolysis of the cellulose to soluble sugars can be carried out with any type of cellulase enzymes suitable for such purpose and effective at the pH and other conditions utilized, regardless of their source. Among the most widely studied, characterized and commercially produced cellulases are those obtained from fungi of the genera *Aspergillus, Humicola, Chrysosporium, Melanocarpus, Myceliopthora, Sporotrichum* and *Trichoderma*, and from the bacteria of the genera *Bacillus* and *Thermobifida*. Cellulase produced by the filamentous fungi *Trichoderma longibrachiatum* comprises at least two cellobiohydrolase enzymes termed CBHI and CBHII and at least four EG enzymes. As well, EGI, EGII, EGIII, EGV and EGVI cellulases have been isolated from *Humicola insolens* (see Lynd et al., 2002, Microbiology and Molecular Biology Reviews, 66(3):506-577 for a review of cellulase enzyme systems and Coutinho and Henrissat, 1999, "Carbohydrate-active enzymes: an integrated database approach." In Recent Advances in Carbohydrate Bioengineering, Gilbert, Davies, Henrissat and Svensson eds., The Royal Society of Chemistry, Cambridge, pp. 3-12, each of which are incorporated herein by reference).

In addition to CBH, EG and beta-glucosidase, there are several accessory enzymes that aid in the enzymatic digestion of cellulose (see co-owned WO 2009/026722 (Scott), which is incorporated herein by reference and Harris et al., 2010, Biochemistry, 49:3305-3316). These include EGIV, also known as glycoside hydrolase 61, swollenin, expansin, lucinen and cellulose-induced protein (Cip). Glucose can be enzymatically converted to the dimers gentiobiose, sophorose, laminaribiose and others by beta-glucosidase via transglycosylation reactions.

An appropriate cellulase dosage can be about 1.0 to about 40.0 Filter Paper Units (FPU or IU) per gram of cellulose, or any amount therebetween. The FPU is a standard measurement familiar to those skilled in the art and is defined and measured according to Ghose (Pure and Appl. Chem., 1987, 59:257-268; which is incorporated herein by reference). A preferred cellulase dosage is about 10 to 20 FPU per gram cellulose.

The conversion of cellobiose to glucose is carried out by the enzyme β-glucosidase. By the term "β-glucosidase", it is meant any enzyme that hydrolyzes the glucose dimer, cellobiose, to glucose. The activity of the β-glucosidase enzyme is defined by its activity by the Enzyme Commission as EC#3.2.1.21. The β-glucosidase enzyme may come from various sources; however, in all cases, the β-glucosidase enzyme can hydrolyze cellobiose to glucose. The β-glucosidase enzyme may be a Family 1 or Family 3 glycoside hydrolase, although other family members may be used in the practice of this invention. The preferred β-glucosidase enzyme for use in this invention is the Bgl1 protein from *Trichoderma reesei*. It is also contemplated that the β-glucosidase enzyme may be modified to include a cellulose binding domain, thereby allowing this enzyme to bind to cellulose.

Cellulase enzymes can be added to the aqueous feedstock slurry prior to or during its introduction in the unmixed hydrolysis reactor or to the unmixed hydrolysis reactor itself. Examples of methods for adding enzyme include direct injection, which can involve the use of mixing tees; static or non-rotary mixing; or powered, in-line mixing, which can employ in-line rotary devices or in-line shredders. Alternatively, the enzymes may be added directly to the hydrolysis reactor, although the addition of enzymes prior to the introduction of the pretreated feedstock into the hydrolysis reactor is preferred for optimal mixing and for minimizing the energy requirements for mixing. The enzymes may be handled in an aqueous solution or as a powder or granulate.

The enzymatic hydrolysis in the unmixed reactor produces soluble sugars, including glucose oligomers, dimers and/or glucose. The enzyme β-glucosidase can be omitted from the enzyme mixture, although it is preferred to include it during the hydrolysis as the glucose yield is significantly lowered in its absence.

The flow of the aqueous feedstock slurry through the reactor can be upward or downward. That is, the aqueous slurry can be introduced at the bottom of the hydrolysis reactor with a net upward flow or it can be introduced at the top of the reactor and flow downwardly. If the aqueous slurry flows upwardly in the reactor, the solids particles will not flow upwardly more slowly than the liquor due to the relatively high consistency of the slurry.

Without being limiting, the slurry may move in plug flow through the unmixed hydrolysis reactor. However, it should be appreciated that, in practice, the plug flow of the aqueous slurry through the reactor will not be ideal as some channeling or laminar flow of the aqueous feedstock slurry can occur as it moves through the reactor.

As used herein, a "plug flow reactor" is an upflow, downflow or horizontal reactor that is designed so as to achieve a plug flow of reactor contents. As discussed above, the plug flow may not be ideal, but there is no significant differential retention of solids with respect to liquid in the slurry.

Moreover, some partial mixing or other perturbation of the reactor contents may occur as the material is discharged, for example by a bottom mounted rotary scraper. However, in the reaction zone of an unmixed reactor, there will be no or very limited slurry movement in the radial direction. As used herein, the term "reaction zone" refers to a zone in the unmixed hydrolysis reactor that excludes the volume of the reactor measured from the top of the reactor to 90% of the reactor height and the volume of the reactor measured from its bottom to a location that is 10% of the reactor height.

The enzymatic hydrolysis is generally conducted at a pH between about 4.0 and 6.0 as this is within the optimal pH range of most cellulases. This includes ranges therebetween having numerical limits of 4.0, 4.25, 4.5, 4.75, 5.0, 5.25, 5.5, 5.75 or 6.0. When the pH of the pretreated cellulosic feedstock is acidic, its pH will typically be increased with alkali to about pH 4.0 to about 6.0 prior to enzymatic hydrolysis, or more typically between about 4.5 and about 5.5. However, cellulases with pH optima at more acidic and more alkaline pH values are known.

The alkali can be added to the pretreated feedstock after it is cooled, before cooling, or at points both before and after cooling. The point of alkali addition can coincide with the cellulase enzyme addition, or the addition point can be upstream or downstream of the location of the enzyme addition. If the enzyme is added upstream of the alkali addition point, the contact time of the enzyme at the lower pH of the pretreated feedstock would typically be minimized to avoid enzyme inactivation. Without being limiting, it is preferred that alkali is added prior to enzyme addition or simultaneously therewith.

The alkali may be added in-line to the pretreated feedstock, such as to an in-line mixer, to a pump downstream of pretreatment or directly to the unmixed reactor. A pump that comprises chemical injection ports, and that promotes mixing, such as medium consistency pump, can be employed to disperse alkali and enzyme simultaneously. Without being limiting, an in-line mixing device could be employed to add alkali and enzyme separately.

The temperature of the slurry is adjusted so that it is within the optimum range for the activity of the cellulase enzymes. Generally, a temperature of about 45° C. to about 70° C., or about 45° C. to about 65° C., or any temperature therebetween, is suitable for most cellulase enzymes. For example, the temperature of the slurry may be adjusted to about 45, 46, 47, 48, 49, 50, 51, 52, 53, 54, 55, 56, 57, 58, 59, 60, 61, 62, 63, 64 or 65° C. However, the temperature of the slurry may be higher for thermophilic cellulase enzymes.

In order to maintain the desired hydrolysis temperature, the hydrolysis reactors may be jacketed with steam, hot water, or other heat sources. Moreover the reactors may be insulated to retain heat.

The hydraulic residence time in the unmixed reactor may be between 2 and 36 hours, between 4 and 24 hours or between 6 and 12 hours. The upper limit of this range is generally limited by flow instability.

It is preferred that enzymatic hydrolysis and fermentation are conducted in separate vessels so that each biological reaction can occur at its respective optimal temperature. However, the unmixed hydrolysis and the mixed hydrolysis described below may be conducted simultaneously with fermentation in a simultaneous saccharification and fermentation. SSF is typically carried out at temperatures of 35-38° C., which is a compromise between the 50° C. optimum for cellulase and the 28° C. optimum for yeast. Consequently, this intermediate temperature can lead to substandard performance by both the cellulase enzymes and the yeast.

According to one embodiment of the invention, after completion of the unmixed hydrolysis, the percent conversion of the cellulose in the mixture of partially hydrolyzed cellulose is between about 10 wt % and about 70 wt %, or between about 15 wt % and about 65 wt %, or between about 10 wt % and about 50 wt %, or between 10 wt % and about 40 wt %, or any value therebetween, including ranges having numerical limits of 10, 15, 20, 25, 30, 35, 40, 45, 50, 55, 60, 65 or 70 wt %. The percent hydrolysis of the cellulose in this mixture is measured according to the method of Example 2 and is measured at the outlet of the unmixed hydrolysis reactor or, if a system of unmixed hydrolysis reactors is employed, at the outlet of the last reactor in the system.

The partially hydrolyzed cellulose may be withdrawn from the unmixed reactor by any suitable device known to those of ordinary skill in the art. Without being limiting, in those embodiments employing an unmixed downflow reactor, the reactor contents may be conveyed out of the reactor by a discharge screw aided by a rotary bottom scraper. As would be appreciated by those of ordinary skill in the art, other devices for discharge of the slurry could be utilized. For example, the bottom of an unmixed downflow reactor may be conical in shape to facilitate discharge of the reactor contents. This latter embodiment is suitable for thinner slurries, while the bottom mounted scraper can remove slurries of higher consistency.

In those embodiments employing an unmixed upflow reactor, a sweep arm may be located at the top of the reactor to sweep the partially hydrolyzed cellulose into a side-mounted chute or pipe. This particular embodiment is suitable if the reactor contents are relatively thick. For thinner material, the top of the reactor can be conical in shape to facilitate withdrawal of the partially hydrolyzed cellulose into a pipe mounted on the top of the reactor.

The viscosity of the reactor contents, and thus the specific means utilized for withdrawal of reactor contents, will vary with the retention time in the unmixed reactor, the enzyme concentration and other factors.

The mixture of partially hydrolyzed cellulose resulting from the unmixed hydrolysis may resemble a plug of material, or the consistency may be such that it resembles an aqueous slurry. As used herein, the term "aqueous slurry" refers to either a pretreated feedstock that resembles an aqueous slurry or a mixture of partially hydrolyzed cellulose that resembles a plug of material.

Hydrolysis with Mixing

The mixture of partially hydrolyzed cellulose from the unmixed hydrolysis is introduced to one or more hydrolysis reactors that effect mixing of the slurry. Typically, the slurry is introduced into a mixed hydrolysis reactor by a pump.

Figure 1A:
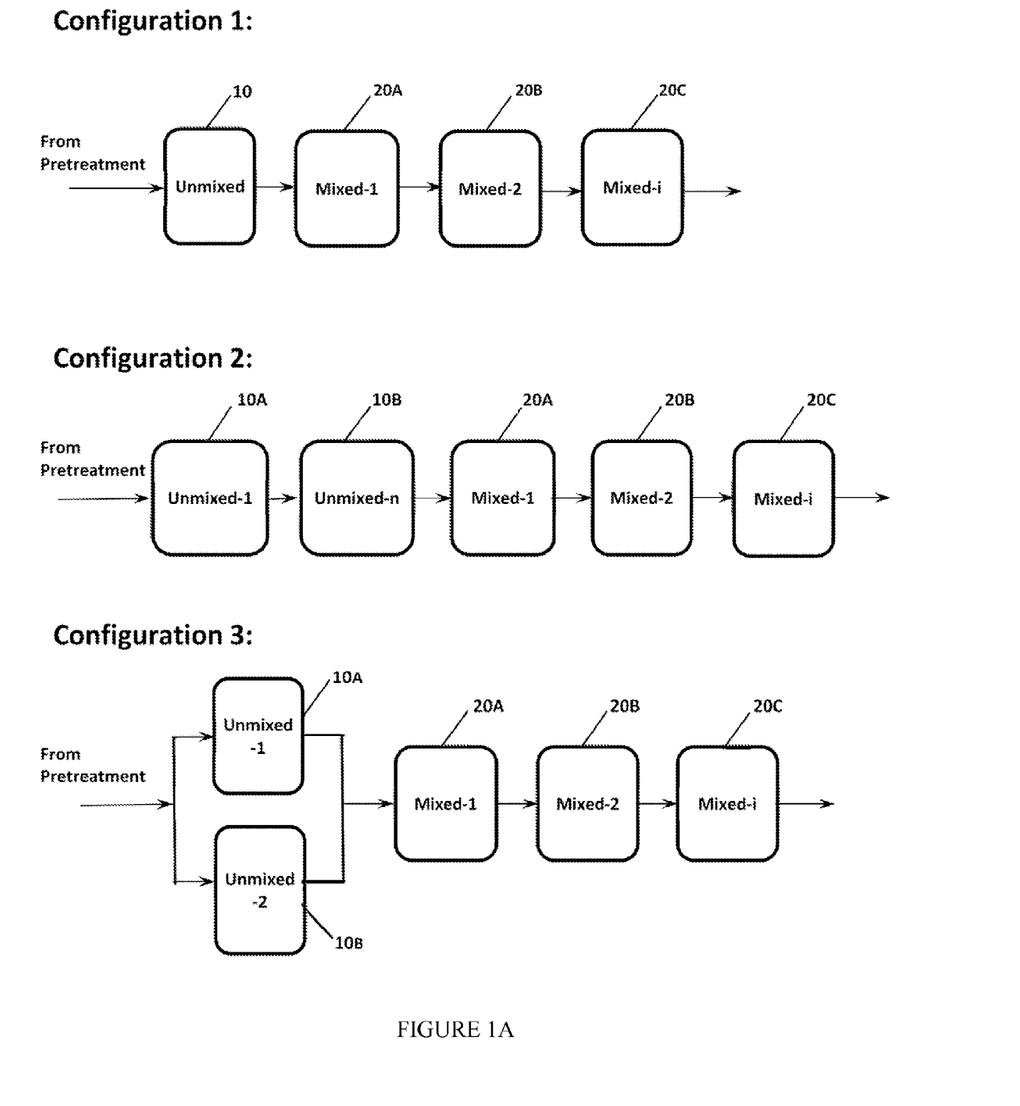
FIGS. 1A and 1B show several configurations of cellulose hydrolysis systems comprising unmixed and mixed hydrolysis reactors.
Figure 1B:
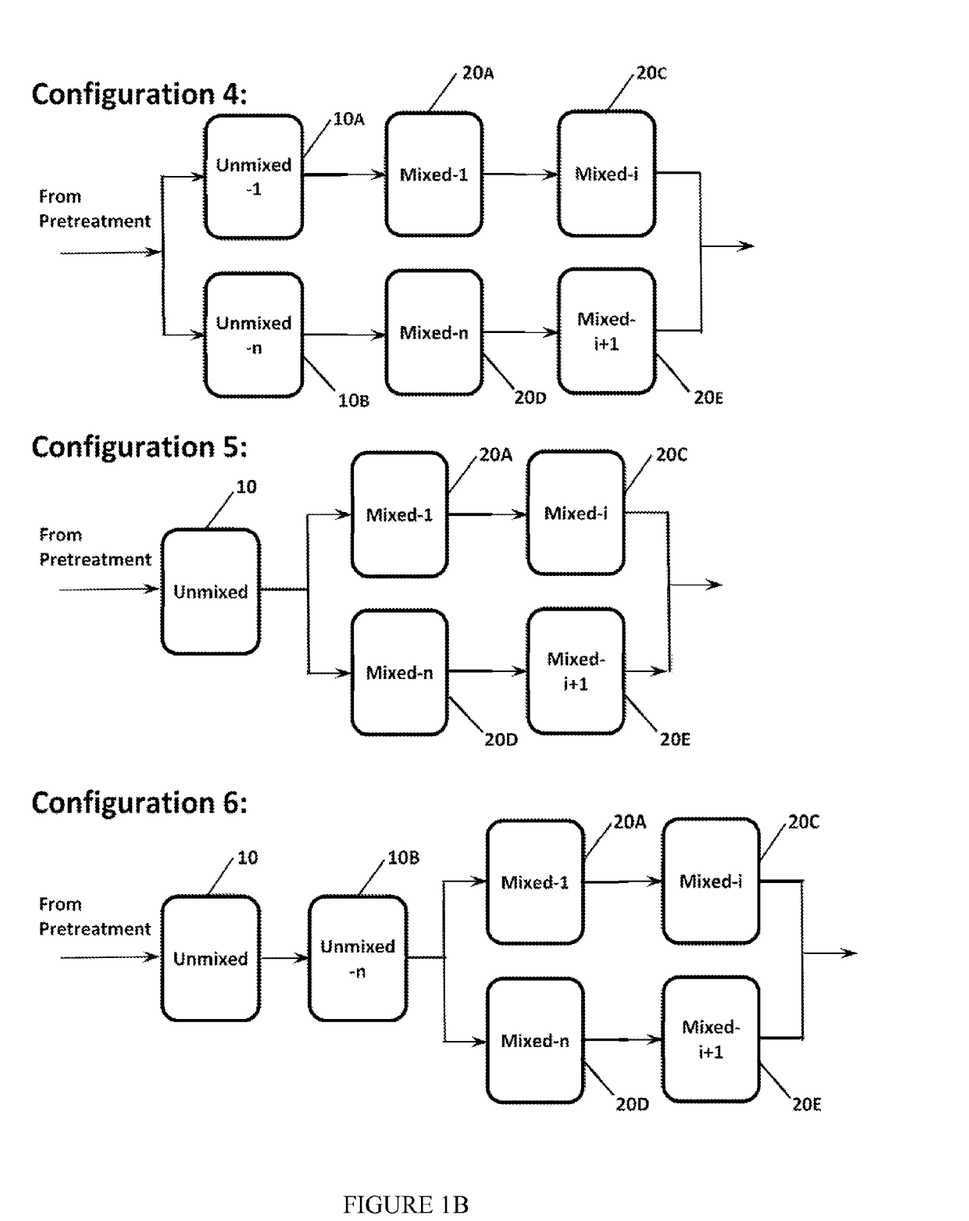

Various exemplary configurations of unmixed and mixed reactors in parallel, series and combinations thereof that can be employed in accordance with the invention are depicted in FIG. 1A. Configurations 1 and 2 contain unmixed and mixed reactors in series. In configuration 1 of FIG. 1A, an unmixed reactor 10 is followed by mixed reactors 1 and 2, denoted 20A and 20B, which in turn can be followed by any number of additional mixed reactors in series 20C. Configuration 2 is essentially the same as configuration 1, except for the provision of additional unmixed reactor 10B in series upstream of the first mixed reactor 20A. Configuration 3 shows two or more unmixed reactors in parallel 10A and 10B with downstream mixed reactors in series 20A, 20B and 20C. In configuration 4 (FIG. 1B), two or more unmixed reactors are in parallel 10A and 10B, with downstream mixed reactors in parallel, denoted 20A, 20C, 20D and 20E. Configuration 5 contains an unmixed reactor 10, followed by mixed reactors in parallel 20A, 20C, 20D and 20E. In configuration 6, two or more unmixed reactors are shown in series, denoted 10 and 10B, followed by mixed reactors in parallel 20A, 20C, 20D and 20E.

Mixing in the mixed hydrolysis reactor(s) may be achieved by any conventional means, including mechanical mixers such as top-mounted, side-mounted, or bottom-mounted impellers, agitators or eductors; rapid movement of liquid slurry streams pumped into or through the vessel; and/or introducing or generating gases or vapours in the vessel.

A particularly suitable mixed hydrolysis reactor is a continuous stirred-tank reactor or CSTR reactor.

Similar to the unmixed hydrolysis, the enzymatic hydrolysis in the mixed hydrolysis is generally conducted at a pH between about 4.0 and 6.0 as this is within the optimal pH range of most cellulases. This includes ranges therebetween having numerical limits of 4.0, 4.25, 4.5, 4.75, 5.0, 5.25, 5.5, 5.75 or 6.0. However, cellulases with pH optima at more acidic and more alkaline pH values are known.

The temperature of the slurry during the mixed hydrolysis is adjusted so that it is within the optimum range for the activity of the cellulase enzymes. Generally, a temperature of about 45° C. to about 70° C., or about 45° C. to about 65° C., or any temperature therebetween, is suitable for most cellulase enzymes. However, the temperature of the slurry may be higher for thermophilic cellulase enzymes.

The mixed hydrolysis reactor(s) may be subjected to light agitation, typically with a maximum power input of up to 0.8 hp/1000 gallons, or may receive heavy agitation of up to 20 hp/1000 gallons.

Optionally, additional cellulase enzyme can be added during the mixed hydrolysis.

When the hydrolysis is carried out in a mixed hydrolysis system that includes multiple mixed hydrolysis reactors, the number of mixed hydrolysis reactors in the system depends on the cost of the reactors, the volume of the aqueous slurry, and other factors. For a commercial-scale plant, the typical number of hydrolysis reactors may be for example, 3 to 12. Preferably, the mixed enzymatic hydrolysis is a continuous process, with continuous feeding of pretreated cellulosic feedstock and withdrawal of the glucose. However, it should be understood that batch and fed-batch processes are also included within the scope of the present invention.

In order to maintain the desired hydrolysis temperature, the contents of the hydrolysis reactor(s) are optionally heated or cooled. Heating or cooling may be carried out with heating or cooling jackets or by heat exchange with re-circulated slurry. The heating or cooling fluid used in the heat exchanger or in the jacket may include steam, hot water, cold water, glycol or brine. It should be understood that the temperature of the reactor contents during the mixed hydrolysis could be maintained within a desired range without any heating or cooling of the reactor contents.

Other design parameters of the mixed hydrolysis system may be adjusted as required. For example, the volume of a mixed hydrolysis reactor in a cellulase hydrolysis system can range from about 100,000 L to about 20,000,000 L, or any volume therebetween, for example, between 200,000 and 5,000,000 L, or any amount therebetween. The total residence time of the slurry in a hydrolysis system may be between about 12 hours to about 200 hours, or any amount therebetween.

After the mixed hydrolysis is complete, the product is glucose and any unreacted cellulose. Insoluble solids present in the resulting stream, including lignin, may be removed using conventional solid-liquid separation techniques prior to any further processing. However, it may be desirable in some circumstances to carry forward both the solids and liquids in the sugar stream for further processing.

According to one embodiment of the invention, between about 75% and about 100% (w/w) of the cellulose in the pretreated feedstock slurry is converted to glucose and/or cellobiose at the completion of the mixed hydrolysis, or between about 85% and about 95%, or any range therebetween. This includes ranges having numerical limits of 75, 80, 85, 90, 95 or 100%. Determination of the cellulose conversion is set forth in Example 2.

Fermentation

Fermentation of glucose resulting from the hydrolysis may produce one or more of the fermentation products selected from an alcohol, a sugar alcohol, an organic acid and a combination thereof.

The fermentation is typically conducted at a pH between about 4.0 and about 6.0, or between about 4.5 and about 6.0. To attain the foregoing pH range for fermentation, it may be necessary to add alkali to the stream comprising glucose.

In one embodiment of the invention, the fermentation product is an alcohol, such as ethanol or butanol. For ethanol production, the fermentation is typically carried out with a *Saccharomyces* spp. yeast. Glucose and any other hexoses present in the sugar stream may be fermented to ethanol by wild-type *Saccharomyces cerevisiae*, although genetically modified yeasts may be employed as well, as discussed below. The ethanol may then be distilled to obtain a concentrated ethanol solution. Butanol may be produced from glucose by a microorganism such as *Clostridium acetobutylicum* and then concentrated by distillation.

Xylose and arabinose that are derived from the hemicelluloses may also be fermented to ethanol by a yeast strain that naturally contains, or has been engineered to contain, the ability to ferment these sugars to ethanol. Examples of microbes that have been genetically modified to ferment xylose include recombinant *Saccharomyces* strains into which has been inserted either (a) the xylose reductase (XR) and xylitol dehydrogenase (XDH) genes from *Pichia stipitis* (U.S. Pat. Nos. 5,789,210, 5,866,382, 6,582,944 and 7,527,927 and European Patent No. 450530) or (b) fungal or bacterial xylose isomerase (XI) gene (U.S. Pat. Nos. 6,475,768 and 7,622,284). Examples of yeasts that have been genetically modified to ferment L-arabinose include, but are not limited to, recombinant *Saccharomyces* strains into which genes from either fungal (U.S. Pat. No. 7,527,951) or bacterial (WO 2008/041840) arabinose metabolic pathways have been inserted.

Organic acids that may be produced during the fermentation include lactic acid, citric acid, ascorbic acid, malic acid, succinic acid, pyruvic acid, hydroxypropanoic acid, itaconoic acid and acetic acid. In a non-limiting example, lactic acid is the fermentation product of interest. The most well-known industrial microorganisms for lactic acid production from glucose are species of the genera *Lactobacillus*, *Bacillus* and *Rhizopus*.

Moreover, xylose and other pentose sugars may be fermented to xylitol by yeast strains selected from the group consisting of *Candida*, *Pichia*, *Pachysolen*, *Hansenula*, *Debaryomyces*, *Kluyveromyces* and *Saccharomyces*. Bacteria are also known to produce xylitol, including *Corynebacterium* sp., *Enterobacter liquefaciens* and *Mycobacterium smegmatis*.

In practice, the fermentation is typically performed at or near the temperature and pH optimum of the fermentation microorganism. A typical temperature range for the fermentation of glucose to ethanol using *Saccharomyces cerevisiae* is between about 25° C. and about 35° C., although the temperature may be higher if the yeast is naturally or genetically modified to be thermostable. The dose of the fermentation microorganism will depend on other factors, such as the activity of the fermentation microorganism, the desired fermentation time, the volume of the reactor and other parameters. It should be appreciated that these parameters may be adjusted as desired by one of skill in the art to achieve optimal fermentation conditions.

The fermentation may also be supplemented with additional nutrients required for the growth of the fermentation microorganism. For example, yeast extract, specific amino acids, phosphate, nitrogen sources, salts, trace elements and vitamins may be added to the hydrolyzate slurry to support their growth.

The fermentation may be conducted in batch, continuous or fed-batch modes with or without agitation. Preferably, the fermentation reactors are agitated lightly with mechanical agitation. A typical, commercial-scale fermentation may be conducted using multiple reactors. The fermentation microorganisms may be recycled back to the fermentor or may be sent to distillation without recycle.

If ethanol or butanol is the fermentation product, the recovery is carried out by distillation, typically with further concentration by molecular sieves or membrane extraction.

The fermentation broth that is sent to distillation is a dilute alcohol solution containing solids, including unconverted cellulose, and any components added during the fermentation to support growth of the microorganisms.

Microorganisms are potentially present during the distillation depending upon whether or not they are recycled during the fermentation. The broth is preferably degassed to remove carbon dioxide and then pumped through one or more distillation columns to separate the alcohol from the other components in the broth. The mode of operation of the distillation system depends on whether the alcohol has a lower or a higher boiling point than water. Most often, the alcohol has a lower boiling point than water, as is the case when ethanol is distilled.

In those embodiments where ethanol is concentrated, the column(s) in the distillation unit is preferably operated in a continuous mode, although it should be understood that batch processes are also encompassed by the present invention. Heat for the distillation process may be introduced at one or more points either by direct steam injection or indirectly via heat exchangers. The distillation unit may contain one or more separate beer and rectifying columns, in which case dilute beer is sent to the beer column where it is partially concentrated. From the beer column, the vapour goes to a rectification column for further purification. Alternatively, a distillation column is employed that comprises an integral enriching or rectification section.

After distillation, the water remaining may be removed from the vapour by a molecular sieve resin, by membrane extraction, or other methods known to those of skill in the art for concentration of ethanol beyond the 95% that is typically achieved by distillation. The vapour may then be condensed and denatured.

An aqueous stream(s) remaining after ethanol distillation and containing solids, referred to herein as "still bottoms", is withdrawn from the bottom of one or more of the column(s) of the distillation unit. This stream will contain inorganic salts, unfermented sugars and organic salts.

When the alcohol has a higher boiling point than water, such as butanol, the distillation is run to remove the water and other volatile compounds from the alcohol. The water vapor exits the top of the distillation column and is known as the "overhead stream".

EXAMPLES

Example 1

Determination of the Undissolved Solids Concentration in a Cellulosic Feedstock Slurry The determination of the undissolved solids (UDS) content is carried out as follows.

A fixed amount of slurry is dispensed into a plastic weigh dish and the slurry weight is recorded accurately using an analytical scale. A filter paper circle, appropriately sized for a Buchner funnel, is placed in an aluminum weighing tin and the combined weight of the tin and filter paper is recorded. After transferring the pre-weighed filter paper to the Buchner funnel, the pre-weighed slurry is passed through the filter paper to isolate the solids. Small volumes of de-ionized water are used to ensure that the solids are quantitatively transferred from the weigh dish to the Buchner funnel. The solids are then washed using excess deionized water, after which the washed sample and filter paper are transferred into the pre-weighed aluminum tin. Care should be taken to ensure the solids are quantitatively transferred. After drying the aluminum tin in a 105° C. oven overnight, the contents are weighed accurately and the UDS is quantified by determining, as a percent, the number of grams of dry solids per gram of slurry.

Example 2

Determination of the Degree of Conversion of Cellulose after Unmixed or Mixed Hydrolysis The degree of cellulose conversion is determined by measuring the initial cellulose, glucose and cellobiose concentrations and the concentrations of glucose and cellobiose after unmixed or mixed hydrolysis has taken place, and applying the following equations.

$$X = \left[\frac{(G - G_o) + 1.053(G_2 - G_{2o})}{G_{max}}\right]100$$

$$G_{max} = \frac{1.11C_o\left[1.02 + 0.041\left(C_o + \frac{X_o}{1000}\right)\right]}{1 - C_o}$$

X=Cellulose conversion (%)
G=Glucose concentration (g/L)
$G_o$=Initial glucose concentration (g/L)
$G_2$=Dimer concentration (g/L); includes primarily cellobiose, but also gentiobiose and other dimers
$G_{2o}$=Initial dimer concentration (g/L); includes primarily cellobiose, but also gentiobiose and other dimers
Gmax=Glucose concentration at 100% cellulose conversion (g/L)
Co=Initial cellulose concentration (%)
Xo=Xylose concentration (g/L)

Example 3

Determination of the Maximum Water Holding Capacity of a Pretreated Cellulosic Feedstock The cellulosic feedstock is pretreated with acid, for example as set forth in U.S. Pat. No. 7,754,457 (incorporated herein by reference). A sample of the pretreated cellulosic feedstock of known dry weight is placed in a container without applying pressure. Water is added gradually to the sample until the point at which additional water added is free water. This point is estimated as the point wherein water forms a thin continuous layer over the cellulosic feedstock. The container is tipped to remove free water. The wet feedstock is then weighed to determine the total amount of water present, including water added and water initially present in the sample. The maximum water holding capacity per mass of dry lignocellulosic feedstock is calculated by dividing the mass of water present in the sample by the dry mass of the feedstock.

The determination of water holding capacity and the percentage of the water holding capacity present in a sample takes into account the presence of dissolved solids in the samples. A detailed calculation is provided below to illustrate how to make such a determination.

A sample of pretreated wheat straw is obtained and the UDS is measured by the procedure set out in Example 1. The UDS is determined to be 22.0%. The sample does not have any free water and is adjusted to pH 5.0 by using 10 M sodium hydroxide prior to the UDS measurement.

The dissolved solids content of the sample is measured by adding 25 g of the sample to 100 mL of deionized water in a 250 mL Erlenmeyer flask at 25° C. and manually shaking the resultant mixture for 30 seconds to disperse the solids throughout the water. The slurry is then filtered over a Fisher or Whatman glass fiber filter. A 2.80 g aliquot of the filtrate is dried overnight in a 105° C. oven. The dry weight is noted, which is 0.0271 g. The dissolved solids content of the sample is then:

$$\frac{0.0271 \text{ g dissolved solids} \left[\frac{100 \text{ g water} + (25 \text{ g sample})}{2.8 \text{ g aqueous}} (78\% \text{ aqueous})\right]}{25 \text{ g sample}} =$$

$$4.63\% \text{ dissolved solids.}$$

The sample of pretreated wheat straw is therefore 22.0% UDS, 4.63% dissolved solids, and 73.37% water (wt %).

The water holding capacity, which takes into account dissolved solids, is then determined as follows. A mass of 5.08 g of the sample is placed in a weigh dish. Water is added to the sample and dispersed throughout the solids until a separate layer of water forms. The separate layer of water is poured off to result in a sample that is at its water holding capacity. The sample is weighed at this point and the weight is 5.87 grams. The water holding capacity of the sample is then:

$$\frac{(5.87 - 5.08)g \text{ water added} + (73.37\%)(5.08)g \text{ water present}}{(5.08 \text{ g sample})(22.0\% \text{ } UDS)} =$$

$$4.04 \text{ g water/g } UDS$$

The sample at 22.0% UDS contains (73.37% water/22.0% UDS)=3.33 g water/g UDS. This sample is at 3.33/4.04=82.5% of the water holding capacity.

Example 4

Hydrolysis of Cellulose Using Unmixed Hydrolysis Followed by Mixed Hydrolysis

Wheat straw was pretreated with sulfuric acid as set forth in U.S. Pat. No. 7,754,457 (incorporated herein by reference). The pretreated feedstock was subsequently hydrolyzed in an unmixed followed by mixed hydrolysis with cellulase enzymes and beta-glucosidase secreted by *Trichoderma reesei* as follows.

The consistency of the pretreated feedstock slurry was increased to 20 wt % undissolved solids (UDS) by filtration. This consistency corresponds to a water content that is 93.2% of the water holding capacity of the pretreated feedstock slurry, as determined by the procedure of Example 3.

The unmixed hydrolysis reaction time was 0 (fully mixed), 4, 8 and 24 hours, after which the hydrolysis was mixed for a total hydrolysis duration time of 73 hours. The experimental conditions for the unmixed and subsequent mixed hydrolysis are shown in Table 1 below.

TABLE 1

| experimental conditions for unmixed hydrolysis followed by mixed | |
|---|---|
| Initial UDS, % | 20% (concentrated by filtration) |
| Batch size | 50 g slurry |
| pH | 5.0 |
| Dosage, mg/g cellulase enzyme | 35 |
| Temperature ° C. | 50 |
| Unmixed hydrolysis time (hr) | 0, 4, 8, or 24 |
| Total hydrolysis time, hr | 73 |
| RPM of Mixed hydrolysis | 250 |

Figure 2A:
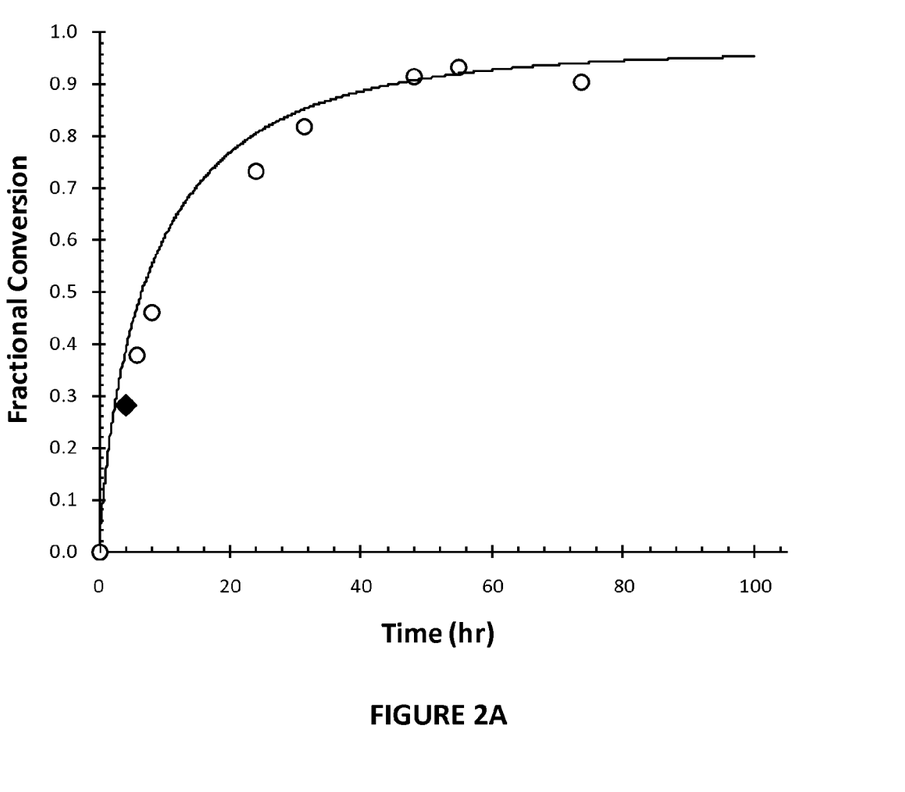
FIG. 2A shows the fractional conversion of cellulose as a function of time (hr) in an unmixed batch hydrolysis followed by mixed batch hydrolysis (symbols) and in a fully batch mixed hydrolysis (curve based on data from a fully mixed hydrolysis). The mixed hydrolysis was commenced after 4 hours of unmixed hydrolysis as depicted by the diamond.
Figure 2B:
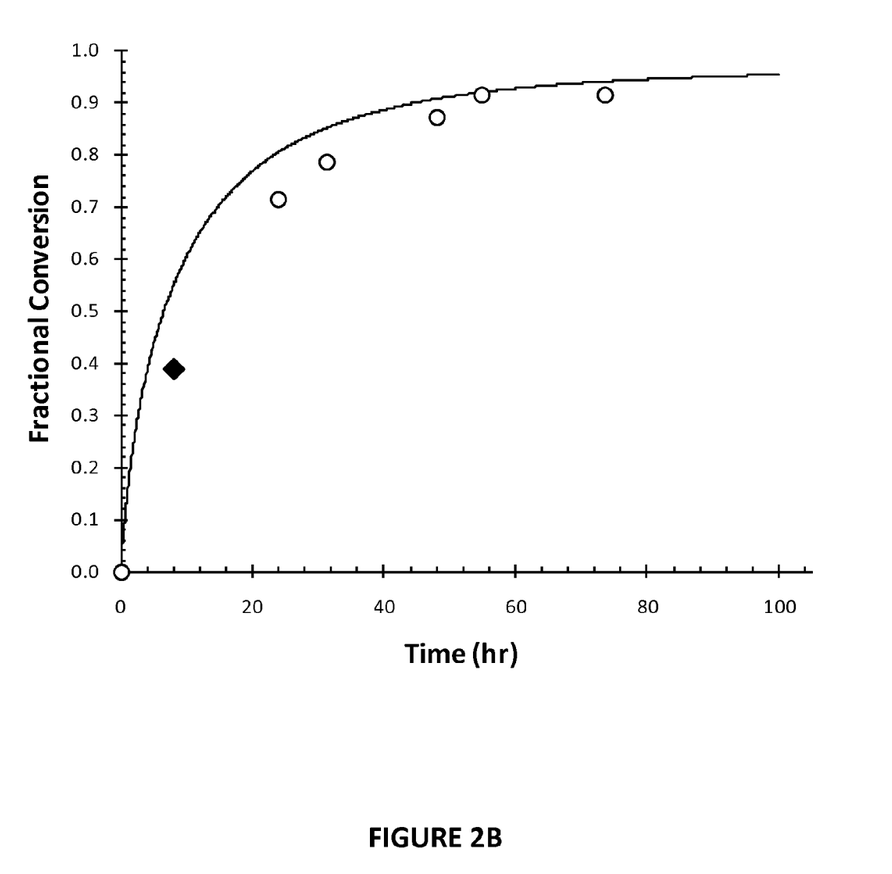
FIG. 2B shows the fractional conversion of cellulose as a function of time (hr) in an unmixed batch hydrolysis followed by mixed batch hydrolysis (symbols) and in a fully mixed batch hydrolysis (curve based on data from a fully mixed hydrolysis). The mixed hydrolysis was commenced after 8 hours of unmixed hydrolysis as depicted by the diamond.
Figure 2C:
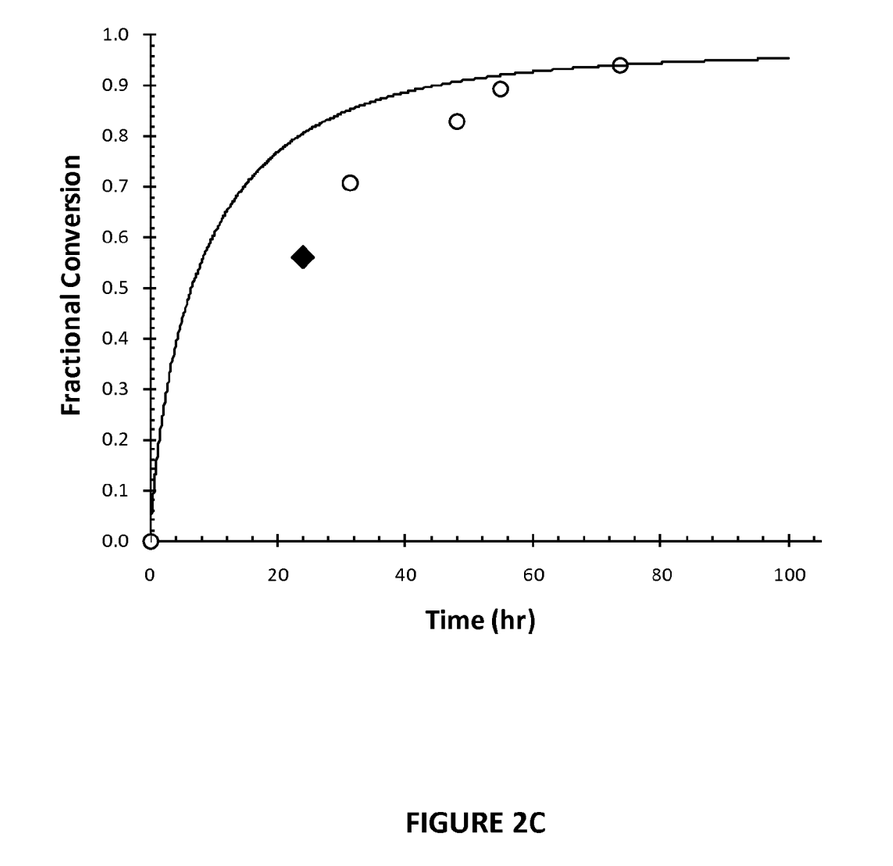
FIG. 2C shows the fractional conversion of cellulose as a function of time (hr) in an unmixed batch hydrolysis followed by mixed batch hydrolysis (symbols) and in a fully mixed batch hydrolysis (curve based on data from a fully mixed hydrolysis). The mixed hydrolysis was commenced at 24 hours of unmixed hydrolysis as depicted by the diamond.

The results of the unmixed hydrolysis followed by mixed hydrolysis are shown in FIGS. 2A, 2B and 2C. The data points in each figure (open circles and filled diamonds) represent the fractional conversion of cellulose for the unmixed followed by mixed hydrolysis at each time point. The time point at which the unmixed hydrolysis was switched to mixed hydrolysis is indicated by a filled diamond. The curves shown in the figures depict the corresponding fully mixed hydrolysis.

FIGS. 2A, 2B and 2C show that the fractional conversion of cellulose achieved at the completion of the hydrolysis, namely 73 hours, was similar for unmixed followed by mixed hydrolysis as for the fully mixed hydrolysis. That is, it is possible to achieve a similar level of conversion after 73 hours in an unmixed/mixed hydrolysis as a hydrolysis in which the contents are mixed throughout the time course. This is beneficial because it indicates that mixing can be avoided for the first 24 hours of hydrolysis without loss of cellulose conversion or glucose production.

Example 5

Unmixed Hydrolysis in an Unmixed Hydrolysis Reactor

Wheat straw was pretreated with acid as set forth in U.S. Pat. No. 7,754,457 (incorporated herein by reference) and then centrifuged in a decanter system to produce a pretreated decanter cake of pretreated feedstock that had a consistency of 24 wt %. The pretreated feedstock was subsequently hydrolyzed with cellulase enzymes and beta-glucosidase secreted by *Trichoderma reesei* in an unmixed hydrolysis reactor as follows.

A fed batch process was used for the unmixed hydrolysis set-up. A defined weight of decanter cake (55 kg) was mixed in a mix tank with an amount of alkali sufficient to achieve a pH of 5 and the resultant mixture was heated to 52° C. Subsequently, an amount of cellulase enzyme to achieve a target enzyme dosage of 60 mg/g was added into the mix tank. The target undissolved solids concentration of 21 wt %. This consistency corresponds to a water content that is 87.6% of the water holding capacity of the pretreated feedstock slurry, as determined by the procedure of Example 3. After a short period of mixing (3 minutes) carried out to disperse the enzyme with the slurry, the slurry was transferred to a 600 L unmixed hydrolysis reactor with a bottom scraper and a discharge screw and the unmixed hydrolysis was commenced.

The target reaction time for the unmixed hydrolysis was 4 hours. The unmixed reactor was heated with heating tapes to maintain the slurry temperature at 52° C. Four hours after the first batch was fed into the reactor, the hydrolyzed material was withdrawn from the bottom of the reactor continuously. Slurry samples were taken and enzyme in the samples was deactivated immediately.

Figure 3:
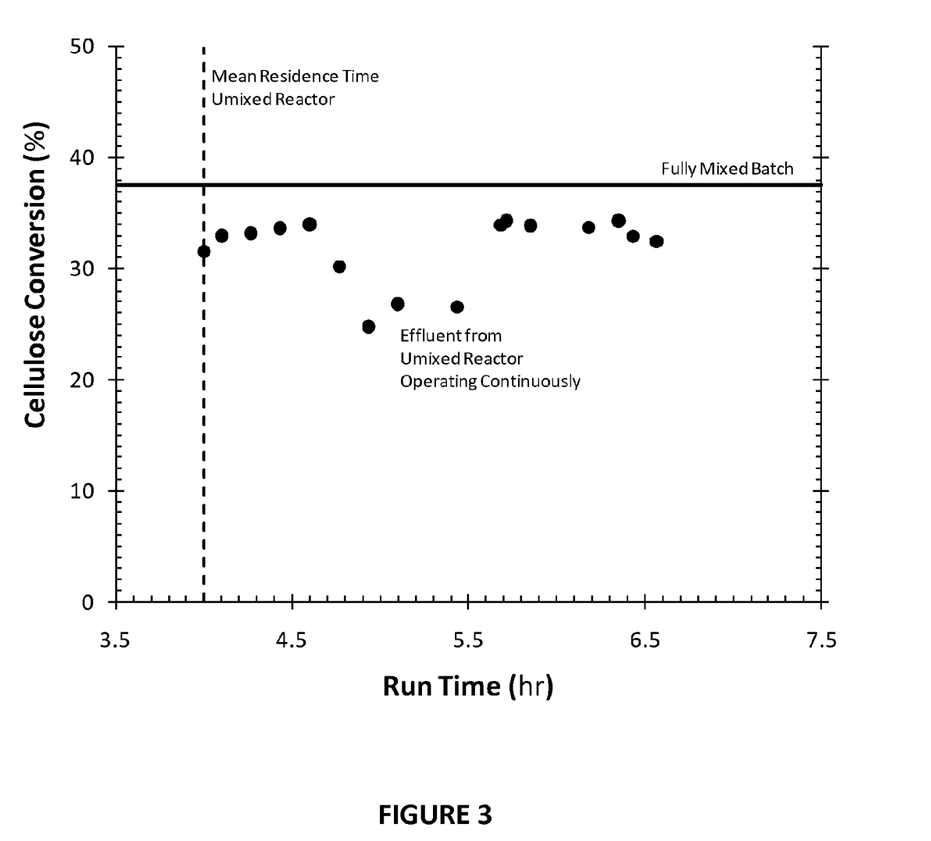
FIG. 3 shows the cellulose conversion (%) for an unmixed hydrolysis conducted in an unmixed hydrolysis reactor (filled circles) and mixed hydrolysis (line) as a function of sampling time.

The results of the unmixed hydrolysis in the 600 L unmixed reactor are presented in FIG. 3 (filled circles), along with a mixed cellulose conversion, depicted as the line above the data points. As shown in FIG. 3, the percent of cellulose conversion for the hydrolysis carried out in the unmixed reactor approaches the cellulose conversion achieved with the fully mixed hydrolysis.

Example 6

Comparison of Power Consumption in Unmixed Hydrolysis Followed by Mixed Hydrolysis Versus a Fully Mixed Hydrolysis A conventionally designed 20 L mixed tank was equipped with industrial standard hydrofoils and operated in batch mode. Power draw was determined by on-line measurement of the shaft torque. The mixed tank was operated with 18.8 L of slurry and the temperature maintained at 50° C. The power requirement was defined such that full motion was observed at four locations at the walls of the tank; bottom, two sides (180° apart) and the top. This ensured that the there was no significant stagnation of the slurry at any visible location in the tank with an approximate 1 cm/s velocity at the walls. To reach this condition, the agitator power was set to achieve a specific RPM, held for 10 minutes, then observations taken. If visible stagnation was observed at the walls, the power was further increased and the process repeated until full motion was observed.

The pretreated feedstock has an initial UDS of 20 wt %, which corresponds to a water content that is 93.2% of the water holding capacity of the pretreated feedstock as determined by the procedure set forth in Example 3.

Figure 4:
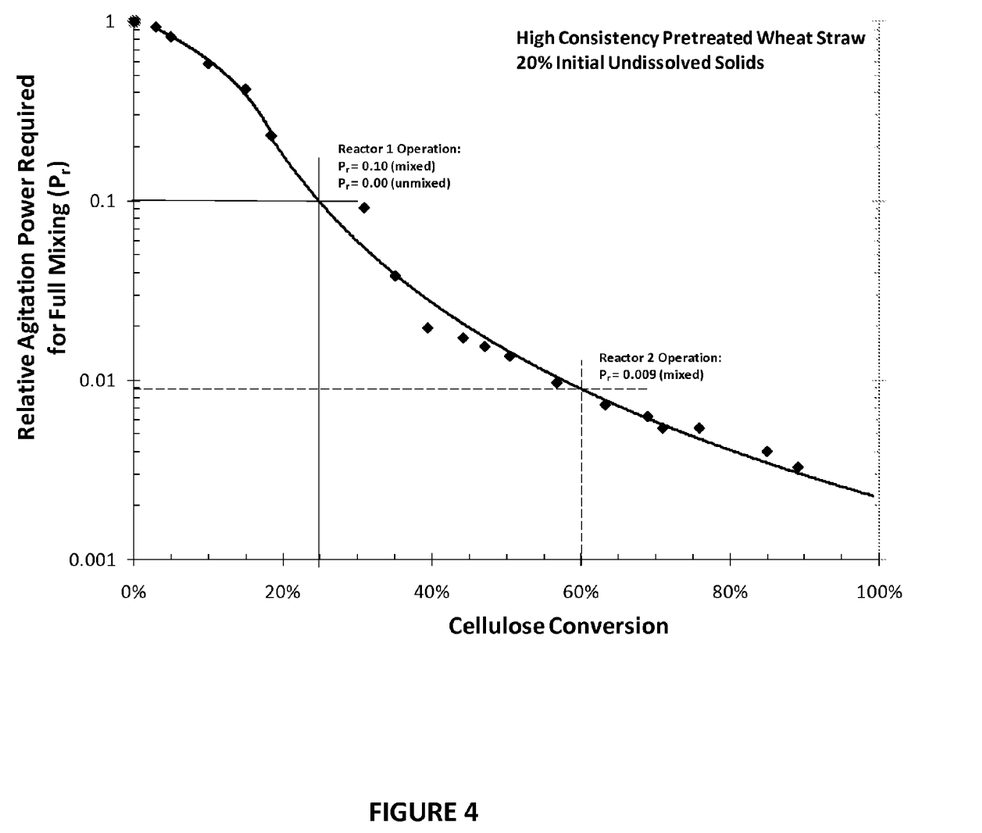
FIG. 4 shows the relative agitation power required for full mixing as a function of the cellulose conversion for a pretreated feedstock having 20% initial undissolved solids (UDS), which corresponds to a water content that is 93.2% of the water holding capacity of the pretreated feedstock as determined by the procedure set forth herein.

It is known (Levenspiel, 1999, Chemical Reaction Engineering, Third Edition, John Wiley and Sons, Chapter 5) that in a constant density system, an ideal unmixed reactor (plug flow) is more efficient than an ideal mixed (CSTR) and that an unmixed plug flow reactor is well approximated by a batch reactor. Therefore, it was assumed that a four hour unmixed stage is approximately equal in tank volume to a four hour mixed tank to achieve the same output yield. The results in FIG. 4 show that for a mixed first stage hydrolysis with cellulose conversion of 25%, relative power consumption is approximately 10% of the amount required to agitate the initial slurry prior to enzyme addition. By comparison, for an unmixed first reactor, relative power consumption is approximately zero. When the system employs two or more mixed reactors in series, total power consumption will be lower when an unmixed reactor(s) is/are used upstream of the mixed reactors. For example, if the initial slurry, prior to enzyme addition, required 100 HP/1000 gal to fully mix, then the first mixed reactor requires 10 HP/1000 gal, and the unmixed reactor would require 0 HP/1000 gal. For a 1000 gal series of two mixed reactors, the total power requirement would be 10 HP+0.9 HP=10.9 HP, whereas for an unmixed reactor in series with a mixed reactor the total power requirement would be 0 HP+0.9 HP=0.9 HP, which is approximately a 92% power savings, while maintaining the final targeted cellulose conversion. While not prohibitive, the use of conventional mixing equipment in the first mixed stage of this example would result in excessive motor sizes at commercial scales. The inclusion of an unmixed reactor greatly diminishes the motor size constraints and permits for conventional mixing equipment to be applied in all mixed tanks, which simplifies the design.

It should be appreciated that the Examples are for illustrative purposes only and should not be construed to limit the current invention in any manner.

The invention claimed is:

1. A process for the enzymatic hydrolysis of cellulose to produce glucose from a pretreated cellulosic feedstock, the process comprising:
 (i) providing an aqueous slurry of the pretreated cellulosic feedstock, which aqueous slurry has an undissolved solids content of between about 12 wt % to about 40 wt %;
 (ii) introducing the aqueous slurry of the pretreated cellulosic feedstock to an unmixed hydrolysis reactor;
 (iii) adding cellulase enzymes to the unmixed hydrolysis reactor before the step of introducing (step ii), during the step of introducing (step ii), or a combination thereof, wherein in the unmixed hydrolysis reactor, the cellulase enzymes hydrolyze a portion of the cellulose to produce soluble sugars and reduce the viscosity of the aqueous slurry, thereby producing a mixture of partially hydrolyzed cellulose containing soluble sugars;
 (iv) continuing the hydrolysis of the cellulose to glucose by feeding the mixture of partially hydrolyzed cellulose containing soluble sugars to a mixed hydrolysis reactor that effects mixing of the mixture or a hydrolysis system comprising mixed hydrolysis reactors that effects mixing of the mixture; and
 (v) withdrawing a stream comprising glucose and unreacted cellulose from the mixed hydrolysis reactor or the hydrolysis system of step (iv), wherein
 the power consumption associated with said process is reduced relative to an otherwise identical process employing a mixed hydrolysis reactor in step (iii).

2. The process of claim 1, wherein the portion of the cellulose hydrolyzed in the unmixed reactor is between about 10 wt % and about 70 wt %.

3. The process of claim 2, wherein the portion of the cellulose hydrolyzed in the unmixed reactor is between about 25 wt % and about 70 wt %.

4. The process of claim 3, wherein the portion of the cellulose hydrolyzed in the unmixed reactor is between about 35 wt % and about 70 wt %.

5. The process of claim 1, wherein the cellulase enzyme contains beta-glucosidase.

6. The process of claim 1, wherein the water content of the aqueous slurry is between about 40% and about 140% of the maximum water holding capacity of the pretreated cellulosic feedstock.

7. The process of claim 6, wherein the water content of the aqueous slurry is between about 60% and about 120% of the maximum water holding capacity of the pretreated cellulosic feedstock.

8. The process of claim 1, wherein the unmixed hydrolysis reactor is a batch, fed-batch or continuous reactor with a height-to-diameter ratio of about 0.2:1.0 to about 5.0:1.0.

9. The process of claim 1, wherein the soluble sugars in the mixture of partially hydrolyzed cellulose comprise glucose, cellobiose, glucose oligomers, or a combination thereof.

10. A process for the enzymatic hydrolysis of cellulose to produce glucose from a pretreated cellulosic feedstock, the process comprising:
   (i) providing an aqueous slurry of the pretreated cellulosic feedstock, which aqueous slurry has an undissolved solids content of between about 12 wt % to about 40 wt %;
   (ii) introducing the aqueous slurry of the pretreated cellulosic feedstock to a system comprising a plurality of unmixed hydrolysis reactors connected in parallel, series or a combination thereof;
   (iii) adding cellulase enzymes to at least one unmixed hydrolysis reactor before the step of introducing (step ii), during the step of introducing (step ii), or a combination thereof, wherein the cellulase enzymes hydrolyze a portion of the cellulose to produce soluble sugars in said at least one unmixed hydrolysis reactor and reduce the viscosity of the aqueous slurry, thereby producing a mixture of partially hydrolyzed cellulose containing soluble sugars;
   (iv) continuing the hydrolysis of the cellulose to glucose by feeding the mixture of partially hydrolyzed cellulose containing soluble sugars to one or more hydrolysis reactors that effect mixing of the mixture; and
   (v) withdrawing a stream comprising glucose and unreacted cellulose from the one or more hydrolysis reactors of step (iv), wherein
   the power consumption associated with said process is reduced relative to an otherwise identical process employing a system of mixed hydrolysis reactors in step (iii).

11. The process of claim 10, wherein the portion of the cellulose hydrolyzed in the unmixed reactor system is between about 10 wt % and about 70 wt %.

12. The process of claim 11, wherein the portion of the cellulose hydrolyzed in the unmixed reactor system is between about 25 wt % and about 70 wt %.

13. The process of claim 12, wherein the portion of the cellulose hydrolyzed in the unmixed reactor system is between about 35 wt % and about 70 wt %.

14. The process of claim 10, wherein the cellulase enzyme contains beta-glucosidase.

15. The process of claim 10, wherein the water content of the aqueous slurry is between about 40% and about 140% of the maximum water holding capacity of the pretreated cellulosic feedstock.

16. The process of claim 15, wherein the water content of the aqueous slurry is between about 60% and about 120% of the maximum water holding capacity of the pretreated cellulosic feedstock.

17. The process of claim 11, wherein the unmixed hydrolysis reactors are batch, fed-batch or continuous reactors with a height-to-diameter ratio of about 0.2:1.0 to about 5.0:1.0.

18. The process of claim 10, wherein the soluble sugars in the mixture of partially hydrolyzed cellulose comprise glucose, cellobiose, gentiobiose, glucose oligomers, or a combination thereof.

19. A process for the enzymatic hydrolysis of cellulose to produce glucose from a pretreated cellulosic feedstock, the process comprising:
   (i) hydrolyzing the pretreated cellulosic feedstock having an undissolved solids content of between about 12 wt % to about 40 wt % with cellulase enzymes in at least one unmixed hydrolysis reactor to produce a mixture comprising partially hydrolyzed cellulose, wherein during said hydrolyzing between about 10 wt % to about 70 wt % of the cellulose is hydrolyzed; and
   (ii) further enzymatically hydrolyzing the mixture comprising partially hydrolyzed cellulose and soluble sugars with cellulase enzymes in at least one mixed hydrolysis reactor to produce the glucose, wherein
   the power consumption associated with said process is reduced relative to an otherwise identical process employing at least one mixed hydrolysis reactor in step (i).

20. A process for producing ethanol, the process comprising:
   (i) hydrolyzing a pretreated cellulosic feedstock having an undissolved solids content of between about 12 wt % to about 40 wt % with cellulase enzymes in at least one unmixed hydrolysis reactor to produce a mixture comprising partially hydrolyzed cellulose, wherein during said hydrolyzing between about 10 wt % to about 70 wt % of the cellulose is hydrolyzed;
   (ii) further enzymatically hydrolyzing the mixture comprising partially hydrolyzed cellulose and soluble sugars with cellulase enzymes in at least one mixed hydrolysis reactor to produce glucose, wherein
   the power consumption associated with steps (i) and (ii) is reduced relative to an otherwise identical process employing at least one mixed hydrolysis reactor in step (i); and
   (iii) fermenting the glucose with a microorganism to produce a fermentation broth comprising the ethanol and then concentrating the ethanol.

* * * * *